(12) United States Patent
Auton

(10) Patent No.: US 8,980,623 B2
(45) Date of Patent: *Mar. 17, 2015

(54) CELL CULTURE AND MIXING VESSEL

(75) Inventor: Kevin Andrew Auton, Cambridge (GB)

(73) Assignee: Cellexus Limited, Cambridgeshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/357,534

(22) Filed: Jan. 22, 2009

(65) Prior Publication Data

US 2009/0181452 A1 Jul. 16, 2009

Related U.S. Application Data

(63) Continuation of application No. 11/639,413, filed on Dec. 15, 2006.

(30) Foreign Application Priority Data

Dec. 16, 2005 (GB) .................................. 0525579.9
Sep. 5, 2006 (GB) .................................. 0617490.8

(51) Int. Cl.
*C12M 3/00* (2006.01)
*B01F 3/04* (2006.01)
*B01F 15/00* (2006.01)
*C12M 1/00* (2006.01)

(52) U.S. Cl.
CPC ....... *B01F 3/04113* (2013.01); *B01F 15/00824* (2013.01); *C12M 23/02* (2013.01); *C12M 23/14* (2013.01); *C12M 29/06* (2013.01); *B01F 2003/04134* (2013.01)
USPC .................. 435/296.1; 435/290.1; 435/290.2; 435/290.4; 435/252.8; 261/121.1; 366/101

(58) Field of Classification Search
USPC .......... 435/290.2, 290.4, 290.1, 296.1, 252.8; 210/629; 366/101; 261/121.1
See application file for complete search history.

(56) References Cited

U.S. PATENT DOCUMENTS

| 4,139,457 A | 2/1979 | Mackrle et al. ................. 210/20 |
| 4,142,975 A | 3/1979 | Kinzer ....................... 210/195 R |
| 4,205,133 A * | 5/1980 | Wick ......................... 435/296.1 |
| 4,337,315 A * | 6/1982 | Fukushima et al. ........ 435/296.1 |
| 4,649,117 A * | 3/1987 | Familletti ................... 435/296.1 |

(Continued)

FOREIGN PATENT DOCUMENTS

| EP | 0197299 A1 | 10/1986 | |
| GB | 2 034 683 | 6/1980 | ................ C02F 3/12 |

(Continued)

OTHER PUBLICATIONS

International Search Report for PCT/GB2006/004705, dated May 10, 2007.

(Continued)

*Primary Examiner* — William H Beisner
*Assistant Examiner* — Danielle Henkel
(74) *Attorney, Agent, or Firm* — Morgan, Lewis & Bockius LLP

(57) ABSTRACT

A mixing vessel (10) for containing a liquid, comprises a chamber having a lower chamber portion and an upper chamber portion wider than the lower portion, gas inlet means (14) for supplying gas to the lower portion and means for redirecting rising gas (24), such that, in use, rising gas in the form of bubbles, initially rises substantially vertically and is redirected in a substantially horizontal direction by the means for redirecting rising gas.

24 Claims, 10 Drawing Sheets

(56) References Cited

U.S. PATENT DOCUMENTS

| | | | |
|---|---|---|---|
| 5,081,036 A | | 1/1992 | Familletti |
| 5,443,985 A | * | 8/1995 | Lu et al. ................ 435/393 |
| 6,217,761 B1 | * | 4/2001 | Catanzaro et al. ....... 210/195.4 |
| 2005/0242450 A1 | | 11/2005 | Witheridge ................. 261/77 |

FOREIGN PATENT DOCUMENTS

| | | | | |
|---|---|---|---|---|
| GB | 2 073 243 A | 10/1981 | ............... | C12M 1/04 |
| GB | 2 108 151 A | 5/1983 | ............... | C12M 1/12 |
| JP | 62239979 | 10/1987 | ............... | C12M 1/08 |
| JP | 03160983 | 7/1991 | ............... | C12M 1/08 |
| WO | WO 01/27041 A1 | 4/2001 | ............... | C02F 3/12 |

OTHER PUBLICATIONS

European Search Report in related EP 08171476, dated Jan. 9, 2009.
Office Action in related EP 08171476, mailed Oct. 12, 2012.

* cited by examiner

CELL CULTURE AND MIXING VESSEL

This application is a continuation of U.S. Application Ser. No. 11/639,413, filed Dec. 15, 2006 and claims priority benefit of GB 0525579.9, filed Dec. 16, 2005 and GB 0617490.8, filed Sep. 5, 2006

TECHNICAL FIELD

The invention relates to a mixing vessel suitable for carrying out a cell culture, particularly an aerobic cell culture.

BACKGROUND AND PRIOR ART

Many academic and industrial processes utilise cell culture to generate cells or in the production of biomaterials or compounds of interest.

In other processes, such as ultra filtration or the mixing of biological solutions or the dissolution of solids into aqueous solutions, it is necessary to provide fast, effective and yet gentle mixing of the liquid medium.

In cell culture, an aliquot of cells is placed in a vessel of some description, provided with the nutrients required for the growth of the cells, and is either supplied with oxygen or grown anaerobically in the absence of oxygen. After a period of time to allow production and growth of new cells, the cultured cells are typically removed from a vessel and harvested or separated from the medium.

In processes upstream and/or downstream from the culture process, it is often important to mix cells, media or other materials, to prevent them from settling in a storage tank or from forming precipitates. In these instances, it is essential to keep the medium contained within the vessel from settling and so it is advantageous for the medium in the vessel to be kept in constant motion.

Since the first use of aerobic cell culture systems, there have been a series of physical constraints that workers in the field have attempted to address. One of the primary constraints is how to achieve good aeration of the culture without incurring (excessive) damage to the cells being grown and at the same time to achieve a homogenous suspension, or mixing, of cells and to avoid the formation of unstirred areas or "dead spots".

One arrangement widely used in cell culture employs sparging air in the bottom of a vessel so as to cause recirculation of the culture medium. This further improves aeration without the need for physical agitation and has the added benefit of mixing the cell culture without the need for expensive stirring, rolling or rocking devices. The type of culture system that uses an internal air-powered aeration system is often described as a pressure-cycle fermenter or airlift fermenter.

In a pressure-cycle fermenter, the aerated stream of gas and solution that results from sparging the vessel at its base, has a lower density than that of the undisturbed solution and therefore rises. This stream is often referred to as the "riser". The solution that is drawn in to take its place forms a stream, often referred to the "downcomer". Circulation within the cell culture can therefore be achieved simply by aerating the culture as described in GB2002417A, U.S. Pat. No. 5,660,977 and GB 1383432A.

However this method often suffers from having regions of 'dead zones' in which the culture media is not effectively mixed. To overcome this problem, many inventions have sought to separate the riser and the downcomer through the use of a physical barrier. GB2002417A, U.S. Pat. No. 5,660,977 and GB1383432A describe a variety of configurations in which this is achieved. Generally, the riser is directed to the surface of the culture solution through a tube that is arranged vertically and runs from the bottom, up to just below the surface of the culture medium. The riser moves upwards, and is replaced by the downcomer which circulates the solution. In other arrangements, the downcomer can be an external tube.

Other arrangements. such as that disclosed in U.S. Pat. No. 4,649,117, do not require the use of a separation device to divide the riser and the downcomer. In this arrangement, the upper surface of the culture medium is considerably wider than at the base, which contains the sparger. While this will generate the required riser and downcomer, it can be observed in such systems that there are often areas of the culture that are mixed less well than others to give "dead spots" or "flat spots". To compensate for this, the operator will often increase the aeration rate to achieve better mixing. This is a disadvantage because increased sparging will also give rise to the requirement for more gas, which increases process cost, and greater foaming. Foaming must be controlled, as for certain mammalian cell culture systems, there is a direct correlation between increased sparge rate and increased cell mortality. This trend can be entirely eliminated by controlling foaming through the addition of antifoaming agents. One skilled in the art will recognize that a better solution to this problem is to keep foaming to a minimum so as to reduce the cost of the antifoam addition or the possible interference of the antifoam reagents in downstream processes.

JP61202680A teaches that cells attached to a carrier (generally a bead with an activated surface to which cells adhere) can be kept in suspension in a chamber that is separated from the media feed and mixing apparatus by a porous plate that allows the passage of media and gas but does not allow the carriers, with their adherent cells, from passing through the porous separator plate. This is an advantage because the beads are kept separate from the stirring means, which tend to fragment the beads and therefore loose their ability to bind cells when damaged. However, the porous plate cannot separate cells that are grown in free suspension, which would therefore pass through the porous plate. Therefore JP61202680A is limited in the type of cells which can be successfully grown, and prevent it from being applied in the growth of cells such as insect cells, yeast and bacteria, all of which are grown in suspension and not on surfaces.

The costs of assembling and maintaining such fermentation and cell culture systems in a production environment has always been high and steps have therefore been taken to develop disposable systems made from low-cost plastics. EP 0 343 885 discloses a system that utilises the pressure-cycle principle in a plastics bag, in which the riser and downcomer are separated by an intervening plastics sheet, to promote the pressure-cycle effect. The plastics vessel is sparged using a tube inserted from the top of the plastics vessel and the air is dispersed into small air bubbles through the use of a metallic frit assembly. While the use of a separating sheet may in theory provide better circulation due to the pressure-cycle process, overall, it reduces the amount of mixing that takes place and inevitably causes "dead zones" as mentioned above. A very similar arrangement of a reusable plastics bag with a downward-pointing sparging pipe was described in US 2002/0110915 A1 in which no separator was employed.

Many of the commercially available cell culture systems have relied on the use of some form of impeller, under which the aerating gas is delivered into the cell culture. The speed at which the impeller is rotated, its shape and surface area all have the potential to improve the rate of oxygen transfer. A good summary of the art of impeller design can be found in U.S. Pat. No. 6,250,797. One of the major disadvantages of agitation with impeller blades of any shape is that they cause shear stress and often lead to excessive foaming of the cell culture. Considerable heat can also be generated which must be removed, further increasing costs for production. These issues are to be avoided with non-bacterial cells as this results in lower biomass production and poor cell viability.

Other methods of improving oxygen transfer rates without inducing shear stress as a result of deploying impellers have been developed. For example, flexible plastics bags provide a number of opportunities for alternative means of gentle agitation. Bags can be manipulated through the use of external pressure applied mechanically (U.S. Pat. No. 3,819,158), by moving liquid from one bag chamber to another (EP 972 506 A), from rocking the bag back-and-forth (U.S. Pat. No. 6,190,913) or by moving one portion of the bag using mechanical means with pneumatic collars or cuffs (US 2005/0063250 A). In these cases, it is still often necessary to enrich the airflow into the air space above the culture in order to achieve sufficient rates of oxygen transfer and such systems are only used to grow cells with a low requirement for oxygen.

These issues are not confined to cell culture, but also apply in the preparation of solutions and solids that are used in bio production of all types, or in the isolation of the bio product from the cell culture medium. The use of a disposable modules in such operations significantly reduces the cost of cleaning and revalidation of the plant's components compared with modules made from glass and stainless steel. However, the provision of effective mixing has remained a major challenge for many of the reasons already discussed. Agitation must be achieved either by recalculating a liquid at great velocity, which itself causes problems, or through the inclusion of a disposable propeller driven directly through a sealed bearing system (which must be disposable) or through the use of a magnetically coupled and disposable propeller. Both generate heat, excessive shear forces and are expensive.

SUMMARY OF INVENTION

The invention provides a mixing vessel for containing a liquid, comprising a chamber having a lower chamber portion and an upper chamber portion wider than the lower portion, gas inlet means for supplying gas to the tower portion and redirecting means for redirecting rising gas, such that in use, rising gas in the form of bubbles, initially rises substantially vertically in liquid and is redirected in a substantially horizontal direction by the redirecting means for redirecting rising gas.

Gas introduced into the lower chamber portion rises through the liquid. As the chamber is wider in the upper chamber portion than in the lower chamber portion, introduced gas, preferably sterile gas, rises only through a partial volume of the liquid. This gassified partial volume has a reduced density in relation to the liquid which is not subject to the rising gas. This difference in density can cause liquid in the upper chamber portion to circulate within the upper chamber portion as a result of the introduced gas. Thus circulation pathways which exist completely within the upper chamber portion can be established.

The chamber has a redirecting means for redirecting rising gas so that the rising gas in the form of bubbles is deflected by the redirecting means, and is redirected in a substantially horizontal direction. This movement significantly enhances the circulation within the upper chamber as well as gently disturbing the surface of the liquid, which improves gas transport between the headspace and the liquid surface, when compared with vessels that do not possess this feature.

Conveniently, the redirecting means comprises an abutment inclined with respect to the direction of the rising gas.

The shape of the vessel therefore gives both good aeration of the liquid and mixing of the liquid without the need for mechanical agitation and provides a high surface area of liquid in contact with the headspace above the liquid for further gaseous exchange.

In another aspect, the invention provides a mixing vessel for containing a liquid. comprising a chamber having a lower chamber portion and an upper chamber portion wider than the lower portion, gas inlet means for supplying gas to the lower portion and redirecting means for redirecting rising gas comprising an abutment inclined with respect to the direction of rising gas, such that, in use, rising gas in the form of bubbles, initially rises substantially vertically in liquid and is redirected in a substantially horizontal direction by the abutment.

In another aspect, the invention provides a cell culture vessel comprising a chamber having a lower chamber portion and an upper chamber portion wider than the lower portion and gas inlet means for supplying gas to the lower portion, such that, in use, liquid in the upper chamber portion circulates within the upper chamber portion as a result of the introduced gas.

As well as liquid circulation within the upper chamber portion, some liquid preferably also travels downwardly from the upper chamber portion into the lower chamber portion in a downcomer for subsequent upwards flow under the action of rising gas from the inlet means.

Geometry of Vessel

The chamber typically comprises a back wall, at least a part of which is vertical or substantially vertical (e.g. ±10°), and a front wall. The horizontal distance between the front wall and back wall is referred to as the width of the chamber, which varies with height to constitute the wider upper chamber portion and the narrower lower chamber portion. The back and front walls are typically linked by two side walls which are usually vertical or substantially vertical.

Where the vessel comprises an abutment, it is conveniently inclined relative to the vertical or substantially vertical part of the back wall. In a preferred embodiment, the abutment is a non-vertical part of the back wall. Alternatively the abutment may be a separate component fixed with respect to the vessel.

The gas inlet means preferably extends across substantially the whole length of the back wall and is such that the gas rises close to the back wall. The circulation within the upper chamber portion then typically takes place away from the back wall in a widened region and has a tendency to establish a tubular circulation pattern about a horizontal axis parallel to the back wall.

Thus, in view of the geometry of the vessel, excellent mixing properties are obtained without the need for physical barriers between rising regions of liquid and descending regions of liquid. Thus, preferably any such physical barriers are not present.

The volume of the chamber which is filled with liquid in use is referred to herein as the working volume. The space above the liquid in the chamber constitutes a headspace.

The fill level of the vessel must be selected so that the means for redirecting rising gas, e.g. an abutment, can operate effectively.

Preferably at least part of the back wall is planar for reasons of simplicity of construction. A planar wall has the additional advantage that it can be readily placed in contact with or close to a temperature regulation plate.

The widening of the vessel with respect to height preferably occurs asymmetrically. In other words it is preferable that the lower chamber portion is not centrally located below the upper chamber portion. This further differentiates the current invention from U.S. Pat. No. 4,649,117and others, in which the vessel is essentially symmetrical and usually cylindrical.

Preferably the lower chamber portion is tapered, becoming wider with increasing height, typically having a front wall inclined with respect to the back wall. The angle of taper is conveniently in the range of 5° to 40°, preferably 10° to 30°, e.g. about 20°. This tapered arrangement increases the amount of circulating liquid in the downcomer re-entering the gassified partial volume. Preferably the lower chamber portion is so tapered that it is not undesirably wide at the base thereof. Ideally the lower chamber portion has a width such that the gas inlet means can fit snugly at the base of the vessel. This helps to prevent any dead zones from forming near the base.

Preferably at least a lower part of the upper chamber portion is also tapered, preferably at a more gradual incline than the lower chamber portion, so as to give sufficient width to the upper chamber. This arrangement may be achieved by appropriately varying the angle of inclination of the front wall. The angle of taper is conveniently in the range of from 25° to 80°, preferably 40° to 70°, e.g. 60°. An upper part of the upper chamber is desirably more steeply tapered than the lower part, with the front wall possibly being vertical or even turning back on itself. This arrangement assists with prevention of dead zones and further improves circulation. In other words, the angle of incline of the front wall, has an initial value and with increasing height is followed by a reduction in the incline of at least 0°, preferably at least 20°, which in turn is followed by an increase in the incline of at least 0°, preferably at least 20°. The reduction and increase may be gradual or sudden.

The ratio of the height of the working volume of the chamber to the maximum width of the working volume of the chamber (the aspect ratio) should be appropriately selected to give both good circulation and aeration. A tall chamber has the advantage of having a high hydrostatic pressure at the base as well as a long rise height to the surface for the introduced gas to travel along. Both of these improve the rate of transport of gas into the liquid. An effective chamber should also have sufficient width in the upper chamber portion to provide enough volume for bulk circulation in the upper chamber portion. As a first approximation, the aspect ratio should be no less than 0.5. An aspect ratio of greater than 1.0 is preferred.

If the surface area of liquid in the vessel is A, the rise height of the gas H and the volume of liquid is V, then G=(H×A) / V is preferably greater than 1, preferably greater than 1.2, more preferably greater than 1.5. A typical maximum value of G is 4, although it is preferably less than 3. Ideally G has a value of about 2.

The vessel may be made out of any suitable material, such as glass, metallic materials or polymeric materials, typically being made of glass, steel or plastics materials.

When made out of flexible material, the inner bag may be held on or within a suitable rigid support, or be supported by anchoring the bag to the vessel by a suitable support, although usually, the inner bag is held in position when enclosed by the vessel through a combination of gas pressure inside the bag and the addition of the aqueous solution into the bag.

One skilled in the art will appreciate that the principle of the invention can be applied to vessels with, or without an inner liner bag.

One of the key advantages of the vessel's geometry is that it can be in the form of a disposable bag, typically being supported by a frame fitting the geometry of the vessel. The bag's contents are typically isolated from the environment through the use of suitable filters and may contain an integrated sparging tube that is arranged from left to right along its base. The bag effectively acts as a "liner" being intended for single use and made with plastics materials well suited for this purpose. Thereby, the bag can be replaced, without the supporting frame ever coming into contact with the solutions that the bag contains. In this instance the supporting frame imposes a physical constraint on the flexible bag such that the bag adopts the geometry of the vessel. Advantageously, the bag is slightly oversized so that it pushes into any corners when inflated. The bag is desirably provided in a sterile, pre-validated condition and sealed in packaging. Advantageously, the bag may be made from one or multiple layers of plastics materials which are preferably co-extruded during manufacture and preferably under cleanroom conditions. In this case, preferably at least one of the layers exhibits a high resistance to gas diffusion e.g. nylon or EVA. Another one of these layers may be made from polyethylene which exhibits high resistance to aqueous solution. Preferably any plastics materials used are free from materials derived from animal sources. In a preferred embodiment co-extruded layers are used with the polyethylene layer on an inner face and the other layer(s) on an outer face.

The vessel is typically sealed at the top to prevent ingress of anything which may interfere with a cell culture process or the materials being mixed. The vessel is optionally fitted with a filter, which prevents ingress of external gas and particulates while allowing gas from the airspace to be vented. The gas outlet assembly optionally comprises a pressure regulator, set such that pressure in the headspace may be controlled. Alternatively the headspace may comprise a pressure sensor, the reading of which may be fed to a computer which can be programmed to control the air inlet rate to maintain a fixed headspace pressure.

The vessel may also have one or more additional inlet and outlet ports, arranged at any convenient point around the vessel, e.g. in the headspace or just above the gas inlet means. Any additional inlet and outlet ports may be used for introduction of liquid nutrients or for additional gases or for removing samples. Adding nutrients just above the gas inlet means has the advantage that they will be readily mixed with the bulk of the liquid by the rising gas stream.

Gas Inlet Means

The gas inlet means introduces gas in the form of bubbles which rise upwards through the liquid culture medium in use of the vessel, or the inner bag if this option is adopted. The gas inlet means preferably has a plurality of exit holes which generate a plurality of gas bubbles. The exit holes may be constituted by pores of a porous material such as ceramic material, silicon, porous polymer etc., or by apertures in a solid material such as metal, plastics etc. The size of the exit holes in the gas inlet means conveniently range from 0.1 microns to 1 mm, preferably from 1 to 100 microns. The size of bubbles generated ranges from 0.1 to 2 mm. In a preferred embodiment The gas inlet means delivers gas to the lower chamber portion at any convenient location. Preferably gas is introduced as close to the base of the vessel as possible, although from experimental observations, its precise location does not appear to reduce the efficiency of mixing as long as it is located within the lower quarter of the vessel's height.

It has been found that a gas inlet means which introduces gas over an elongate region is particularly effective at mixing and gaseous exchange. Such an arrangement gives a rising wall of bubbles. This may be achieved by a single elongate gas inlet means with exit holes along its length. Alternatively a sequence of separate inlet devices could be used to the same effect. Because of the tendency of rising bubbles to spread out, an elongate region of rising bubbles could even be achieved when the separate inlet devices are relatively widely spaced. Indeed, experimental observations indicate that effective mixing occurs when the sparging tube occupies no more than 15% of the vessel's width. Separated inlet devices may share a single gas supply if arranged in series, or can each have their own gas supply if arranged in parallel.

The gas inlet means conveniently comprises one or more tubes with gas permeable walls. The shortest distance between tube and the back wall and the shortest distance between the tube and the front wall are preferably both less than 3 times the diameter of the tube. Preferably both distances are no greater than the diameter of the tube.

In a preferred embodiment, the gas inlet means is elongate and made of medical grade polyethylene with a pore size of 20 to 40 microns.

The vessel may be accompanied by a separate controller device, which may be capable of monitoring and controlling various operating parameters such as flow rate, oxygen concentration, headspace pressure etc.

The invention also provides mixing apparatus, particularly cell culture apparatus, including a vessel in accordance with the invention. The apparatus suitably includes appropriate control means, e.g. in the form of a separate controller device.

Use of the Vessel

It has been found to be advantageous to operate a cell culture in the vessel of the present invention with an elevated headspace pressure. This can be achieved by having a means for providing a controllable pressure in gas above the liquid, e.g. by suitable selection of a pressure relief valve and inlet gas flow rate. An elevated pressure has been found to improve the rate of transport of gas into solution. Any gas in the headspace will transfer into the liquid across the top surface of the liquid more rapidly at higher pressure. Additionally the rising gas will also experience the elevated pressure, giving further improvement in gas transport. It is believed that an elevated pressure also helps to prevent or reduce undesirable foam generation at the liquid surface, which is sometimes encountered in cell culture fermentation. A headspace pressure of from 0.01 to 10 psi gauge, preferably from 0.1 to 2 psi gauge conveniently gives the above advantages.

In another aspect, the invention provides a method of performing a cell culture fermentation in a vessel having an enclosed headspace, the method comprising operating at a headspace pressure of from 0.01 to 10 psi gauge, preferably from 0.1 to 2 psi gauge.

Typically the gas to be fed through the gas inlet means contains oxygen. Conveniently compressed air can be fed into the vessel through the gas inlet means, however some cell types may have a greater demand for oxygen than can be delivered with air alone, and so an oxygen-enriched gas may be utilised. The inlet gas is typically sterile.

The inlet gas is normally fed at a continuous steady rate, however for certain applications it may be advantageous to pulse the gas through discontinuously. The rate of pulsing may be selected so as to give optimal mixing. Computer control may be used to regulate intermittent gas flow.

If the vessel has additional gas inlet ports, then a gas of similar or different composition to the gas introduced through the gas inlet means may be used. For example an oxygen/carbon dioxide mixture can be passed through the inlet means in the lower chamber portion and oxygen could be introduced directly into the headspace. This combination would be beneficial for situations where depiction of carbon dioxide is to be avoided whilst maintaining an oxygen rich head space above the liquid so as to give effective oxygenation. A person skilled in the art will appreciate that many other combinations are possible.

The same means for introducing gases for aeration of cell culture systems and the efficient mixing that this generates can also be used to mix other aqueous and non-aqueous solutions, fluids, liquids and solids and suspensions. The ability to gently mix a vessel in this way is a considerable advantage over stirred or rocked systems as it can be readily scaled-up to nearly any working volume, as one skilled in the art will appreciate.

A means for regulating the temperature of the liquid in the vessel is preferably provided. Typically the temperature will be required to be maintained constant within the range of from 5 to 40° C., preferably from 16 to 37° C. for cell culture. Temperature regulation can be implemented by a variety of techniques as will be known to a person skilled in the art of cell culture fermentation. Conveniently, temperature regulation can be achieved by use of a temperature regulation plate in contact with or close to the back wall of the vessel, as mentioned above.

Although the vessel of the present invention has good mixing properties and does not require mechanical agitation, mechanical agitation may additionally be employed if desired or required. This could for example take the form of part of a flexible vessel wall being intermittently deformed, e.g. depressed It is conceivable that a separate impeller means may be present inside the vessel, although this may introduce unhelpful shear forces and is ideally avoided. External manipulation of an inner liner bag may be useful in mixing suspensions of particularly viscous materials.

The geometry of the present invention gives effective mixing and aeration over a wide range of sizes and can, for example, be used with a liquid culture volume of from 1 to 10,000 liters. The vessel may be maintained through manual intervention or under computer control. Suitable sensor means may be provided to monitor appropriate parameters to provide information for control purposes. The invention lends itself particularly well to the use of non-invasive probes with which measurements are recorded by following a fluorescence-based reporter, attached to the inner surface of the vessel such as that taught in U.S. Pat. Nos. 5,037,615 and 5,152,287.

The invention will be further described, by way of illustration, in the accompanying drawings.

DETAILED DESCRIPTION OF THE DRAWINGS

Figure 1:
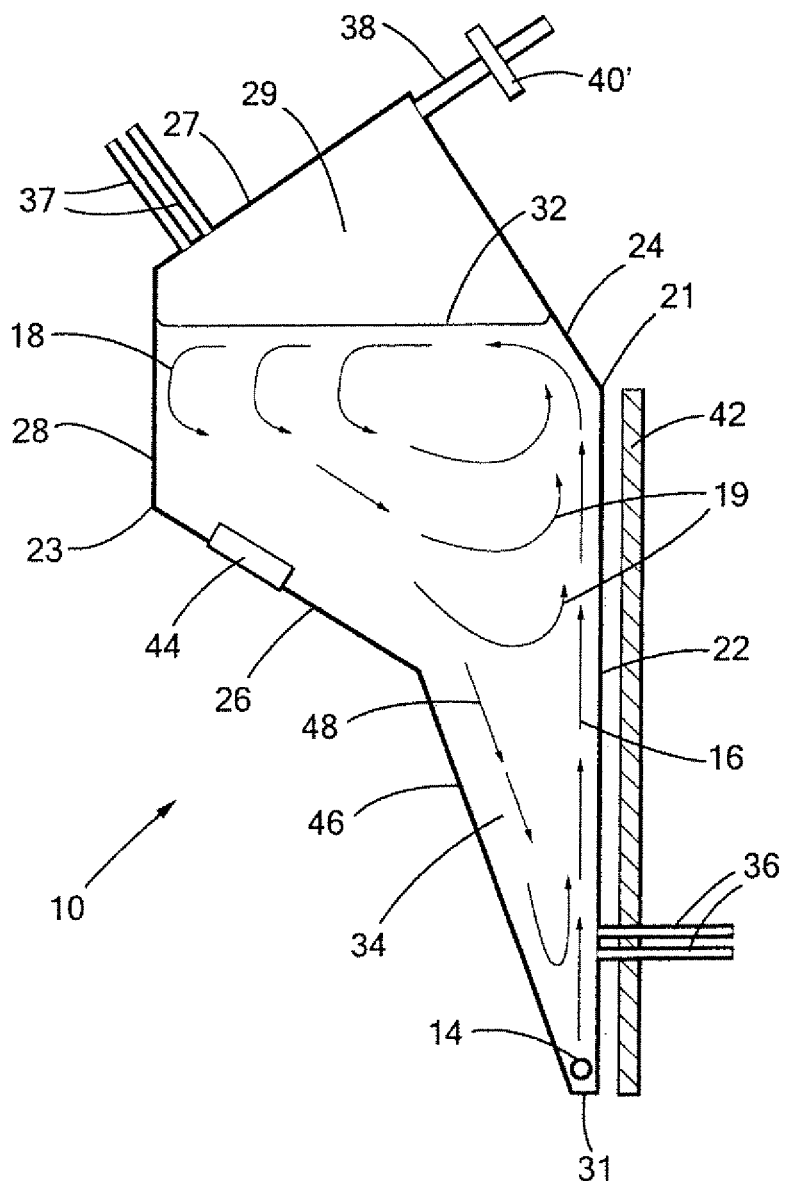
FIG. 1 is a schematic side sectional view of a preferred embodiment of vessel according to the invention.
Figure 2:
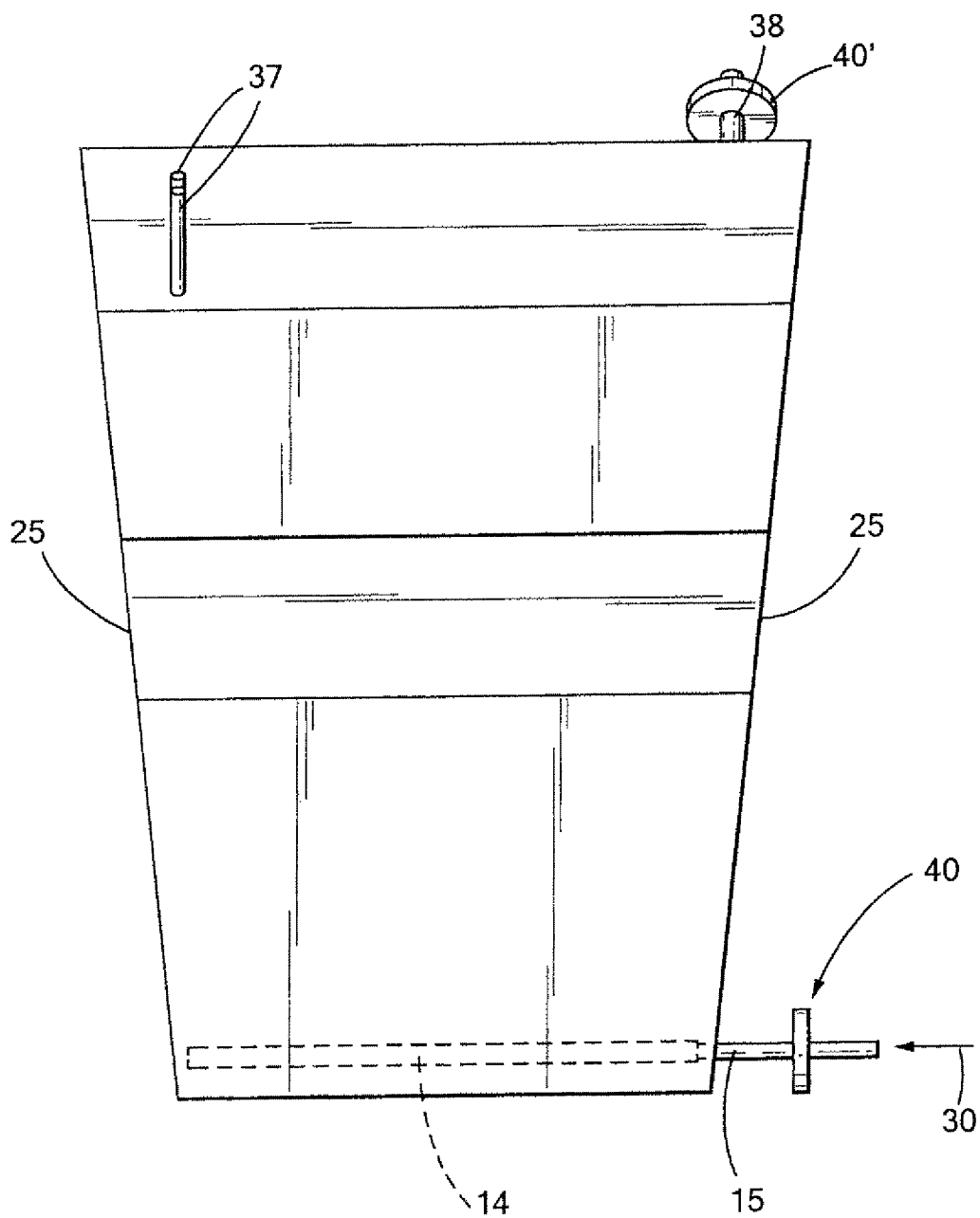
FIG. 2 is a schematic rear view of the vessel shown in FIG. 1.
Figure 3:
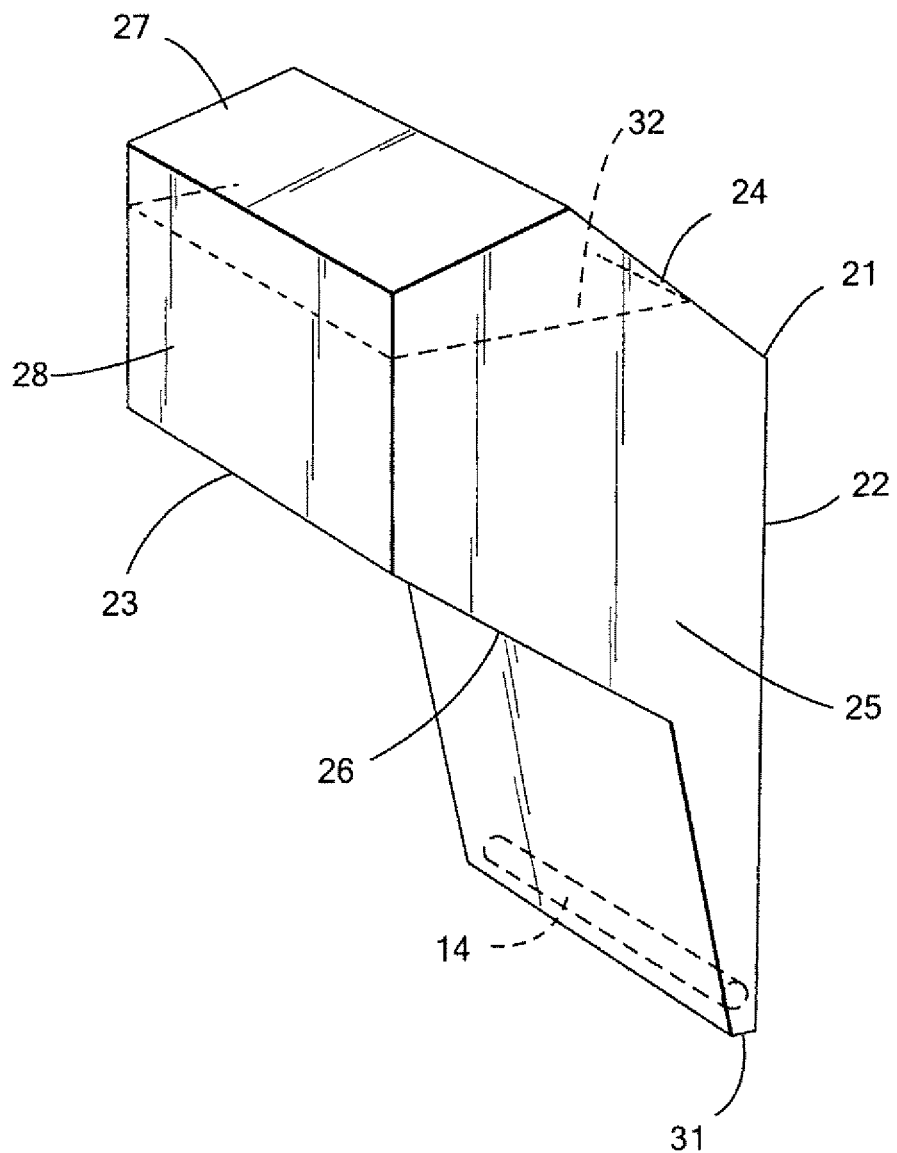
FIG. 3 is a simplified schematic perspective view of the vessel of FIGS. 1 and 2.

FIGS. 1 to 3 show a preferred embodiment of a cell culture vessel 10 according to the invention, containing cell culture medium 34.

The vessel has a back wall 21, a front wall 23, two side walls 25, a top wall 27 and a bottom wall 31 constituting a base of the vessel.

Front wall 23 has a lower portion 46 inclined at about 20° to vertical. The front wall has an upper portion including a lower part 26 inclined at about 60° to vertical and an upper part 28 which is substantially vertical.

The back wall 21 includes a lower part 22 that rises vertically and an upper part 24 that is inwardly inclined at about 32°, constituting an abutment that comprises means for redirecting rising gas.

The vessel contains culture medium 34 which has a top surface 32, the volume of the vessel filled with medium constituting the working volume of the vessel. A headspace 29 is provided above the medium surface.

The lower chamber portion is defined as being between the lower portion 46 of the front wall and the back wall. The upper chamber portion is defined as being between the upper portion of the front wall and the back wall, including the inclined upper part of the back wall beneath the surface of the medium.

The vessel has an overall height of 55 cm and a length at the base of 20 cm. The upper chamber portion has a maximum width of about 22 cm. The vessel has an aspect ratio of about 2 and a G value of about 2, calculated as set out above.

A gas inlet means 14 consists of a porous ceramic tube having an inside diameter of 3 mm and a wall thickness of 2 mm with a pore size range of from 0.1 to 100 microns. The gas inlet means 14 is provided within the lower chamber portion close to the base of the vessel, extending across substantially the entire length of the vessel base. An associated inlet tube 15 leads to the exterior of the vessel, and is provided with an associated filter assembly 40.

Additional inlet ports 36, 37 are provided for addition of liquid reagents and/or gases. A pressure regulation valve 38, set to operate at 2 psi gauge, is provided on the top of the vessel.

A temperature regulation plate 42 is provided slightly spaced from the back wall lower part 22.

A sensor 44 is provided on the lower part 26 of the upper portion of the front wall, which can be used to monitor operating parameters.

The walls of the vessel are made from two layers of co-extruded nylon and polyeshylene with the nylon on the outside, and is free from materials derived from animal sources. The vessel is supported by an outer frame (not shown) or may be a support made of steel, glass or other appropriate materials. The vessel is intended to be disposed of after use and a similar fresh vessel can be used for any subsequent cell culture fermentations or mixing operations. The vessel is initially supplied in sterile pre-validated condition, sealed in packaging.

In use, sterile gas 30 is introduced continuously to gas inlet means 14 via inlet tube 15 from a supply (not shown) at a rate of e.g. 1 liter per minute. Gas bubbles with a size range of from 0.1 to 2 mm are produced and the liquid medium above the gas inlet means 14 rises vertically generally in the direction of arrows 16 (FIG. 1). The rising liquid medium and gas bubbles eventually impinge on the abutment provided by inwardly sloping upper part 24 of the back wall. Liquid medium and gas bubbles are redirected generally in a substantially horizontal direction as represented by arrows 18.

This flow at the culture surface 32 increases the rate of mixing and gas transport from the headspace 29 into the medium 34. Thereafter some of the medium circulates within the upper chamber portion about a horizontal axis as indicated by arrows 18 and 19. Some of the medium flows downwards into the lower chamber portion in a downcomer as indicated by arrows 48, eventually rising again generally in the direction of arrows 16. Thus a tubular circulation pattern is established within the upper chamber portion parallel to the back wall 21.

This arrangement has improved overall aeration and mixing efficiency significantly over other arrangements. It can also be seen from experimental observations that there is effective mixing within the upper chamber, tower chamber, between chambers and from left to right, thus eliminating dead spots without the requirement for over gassing, allowing the operator to achieve high gas mass transfer and mixing at low sparging rates.

The use of water miscible dyes to visualize the currents of solution indicates that there is a highly efficient mixing process in the upper chamber, lower chamber, between the chambers and even from left to right. In experiments, when dye has been introduced at various points throughout the vessel, mixing of an entire vessel, even as large as 50 liters, takes only between 2-5 seconds at relatively low aeration flow rates of 2-3 liters per minute.

Liquid additions may be introduced to the medium via inlet ports 36. An oxygen-enriched sterile air supply, for example, may be introduced to the headspace via inlet ports 37. In another illustration, it may be advantageous to introduce an inert gas such as nitrogen or helium if the vessel is being used to mix liquids, dissolve solids into liquids or maintain suspensions.

An elevated pressure of about 0-2 psi gauge can maintained in the headspace 29 by the action of the pressure regulation valve 38 with the associated filter assembly 40. The medium is maintained at any desired temperature of up to 42° C. by the temperature regulation plate 42.

The medium conditions are maintained for an appropriate time for the desired reactions to take place.

Figure 4:
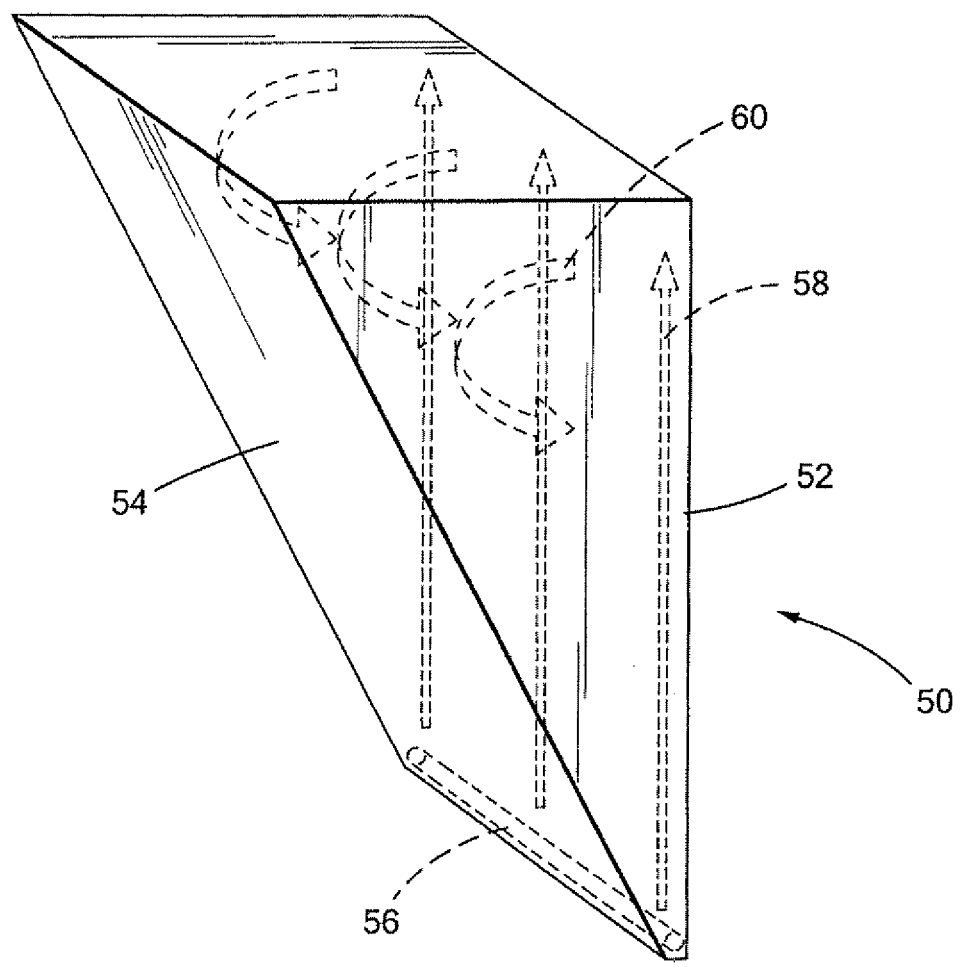
FIG. 4 is a schematic perspective view illustrating another embodiment of a vessel according to the invention.

FIG. 4 shows a simplified schematic representation of another embodiment of the vessel 50 according to the invention omitting the parts of the vessel above the surface of contained liquid, thus showing only the working volume.

The back wall 52 is vertical along its full height. The front wall 54 is a continuously inclined wall from top to base at a constant angle of about 28° to vertical, bounding both the upper chamber portion and the lower chamber portion. The vessel has an aspect ratio of about 2, a G value of about 2, calculated as set out above, and is asymmetric, Gas is introduced through elongate gas inlet means 56, positioned near the base with minimal distance to either the front or back walls. Gas rises vertically as indicated by arrows 58 and the overall reduction in liquid density in this region causes the liquid also to rise in arrow direction 58. Once the liquid reaches the surface its movement becomes substantially horizontal and moves outwards generally in the direction of arrow 60. The liquid circulates generally in the direction of arrow 60 until it rises once more generally in the direction of arrows 58. Thus, liquid circulates within the upper chamber portion.

Figure 5:
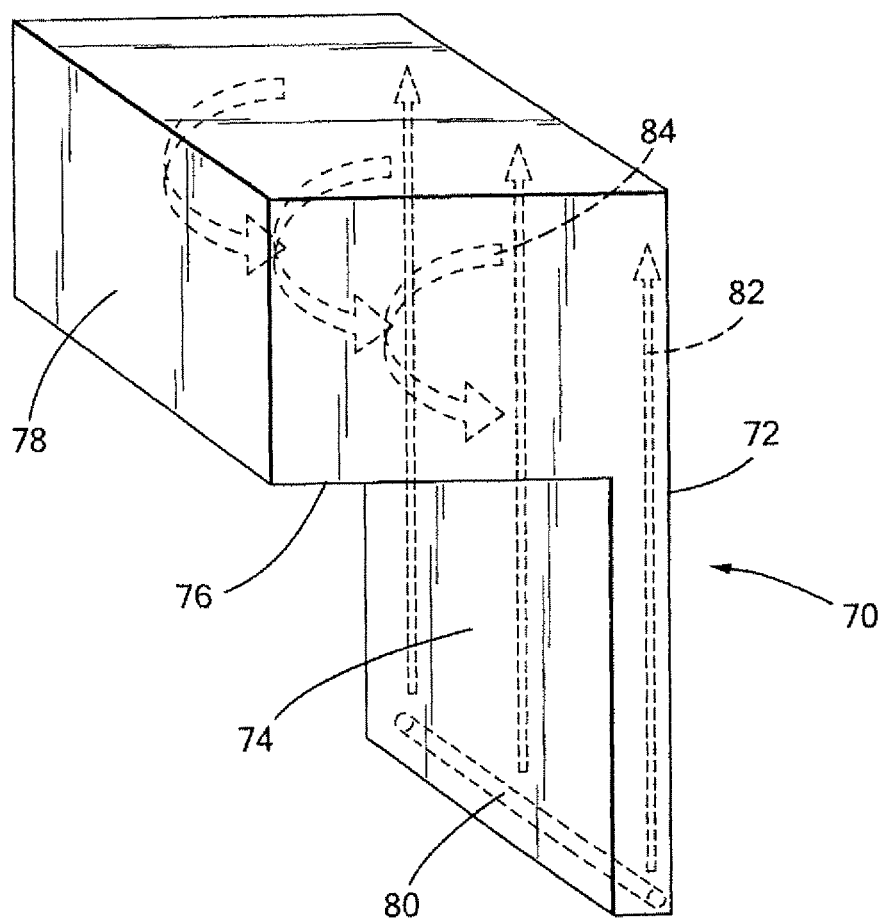
FIG. 5 is another schematic perspective view illustrating a further embodiment of a vessel according to the invention.

FIG. 5 shows a simplified schematic representation of a further embodiment of the vessel 70 according to the invention, similar to that shown in FIG. 4.

The back wall 72 is vertical along its full height. The front wall has a lower portion 74 which rises vertically, a mid portion 76 extending horizontally and an upper portion 78 which also rises vertically. The vessel has an aspect ratio of 2 and a value of about 2, calculated as set out above, and is asymmetric.

Gas is introduced through elongate gas inlet means 80, positioned near the base with minimal distance to the back wall 72. The distance to the front wall 74 is no more than twice the diameter of the gas inlet means 80. Gas rises vertically as indicated by arrows 82 and the overall reduction in liquid density in the region causes the liquid also to rise in arrow direction 82. Once the liquid reaches the surface its movement becomes substantially horizontal and moving outwards generally in the direction of arrows 84. The liquid circulates generally in the direction of arrows 84 until it rises once more generally in the direction of arrows 82. This liquid circulates in the upper chamber portion.

Figure 6:
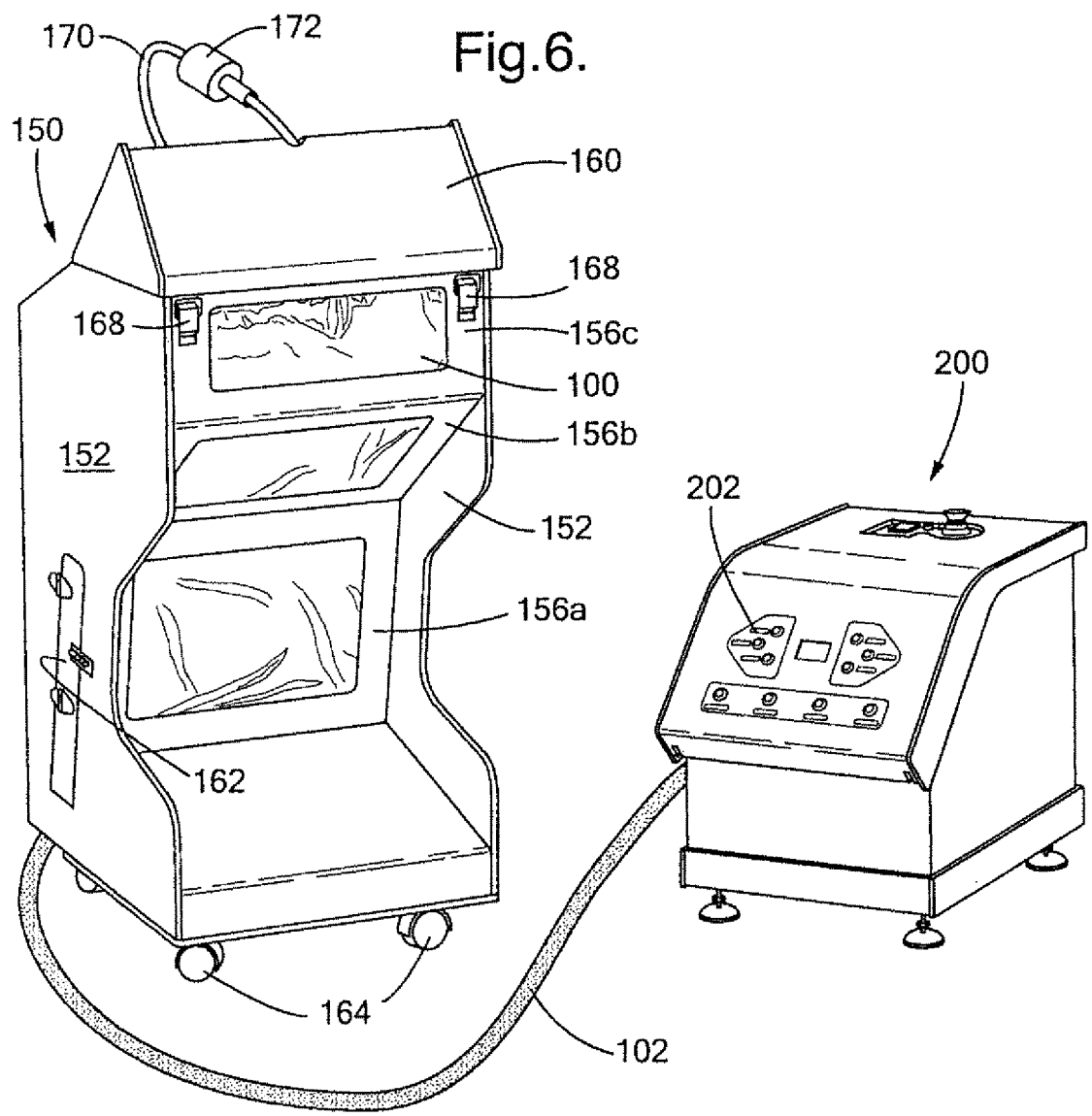
FIG. 6 is a front view of cell culture apparatus including a preferred embodiment of vessel in an associated housing connected to a control unit.
Figure 7:
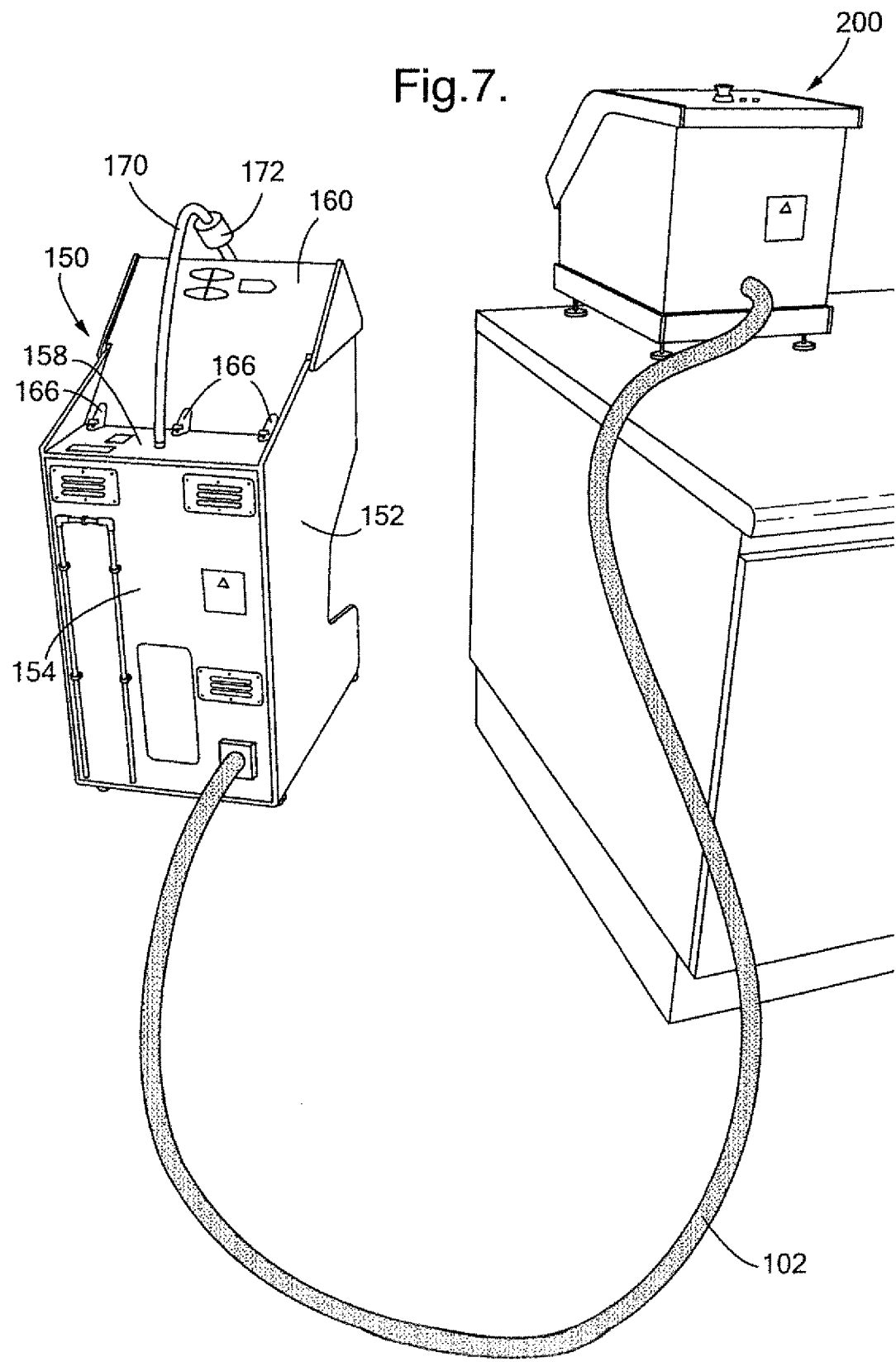
FIG. 7 is a rear view of the arrangement shown in FIG. 6.
Figure 8:
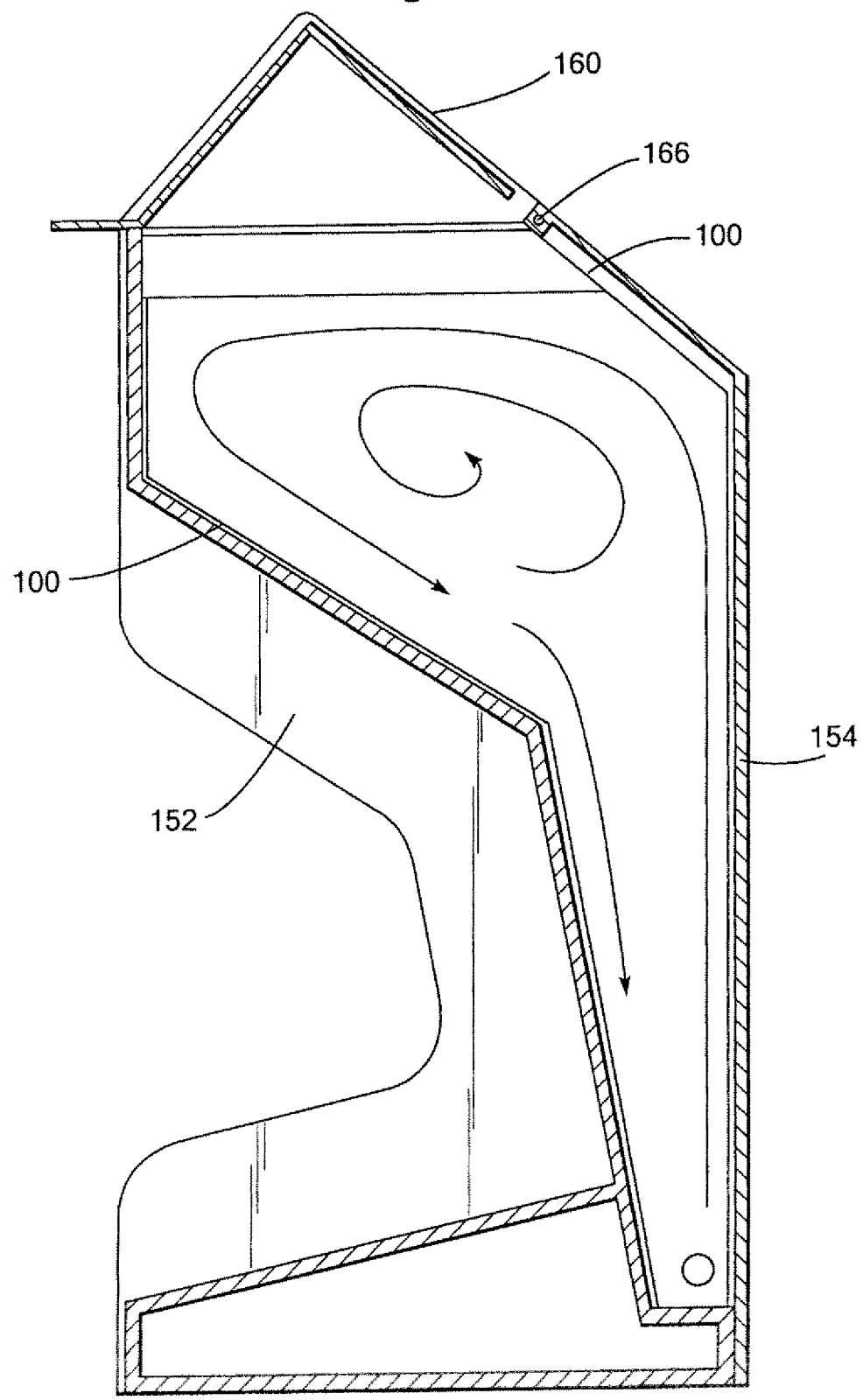
FIG. 8 is a side sectional view of the preferred embodiment of vessel in an associated housing shown in FIGS. 6 and 7.

FIGS. 6 to 8 show cell culture apparatus including a preferred embodiment of a 50 liter vessel 100 in accordance with the invention contained in an associated housing 150 and is connected to a control unit 200 by a gas tube 102.

The vessel 100 is made of transparent flexible plastics material and sits inside the associated housing 150. When filled with liquid the vessel fits snugly and takes the shape of the interior cavity of the housing 150. The vessel 100 is slightly oversized so that it pushes into the corners of the housing 150. The overall geometry of the vessel is similar to that shown in FIGS. 1 to 3 but without tapering sides as shown in FIG. 2.

The housing 150 comprises side walls 152, a rear panel 154, a front wall 156, a top portion 158 and a hinged top lid 160. The housing has a side access door 162 in a side wall 152 for access to entry ports (not shown) in the vessel. The vessel is mounted on wheels 164 for ease of transport and use.

The front wall 156 comprises three panels 156a-c. Each of the panels having a transparent window so that the vessel and its contents can be viewed.

The vessel 100 has a height of 105 cm, a width (distance between front wall 156c and rear panel 154) of 45 cm and a depth (distance between side walls 152) of 62 cm.

The vessel can be accessed by opening the hinged top lid 160. The hinged top lid is attached to the housing by hinges 166 and is held tightly to the top of the housing by clips 168. The vessel comprises a gas outlet tube 170 with an associated filter 172 which passes through a hole in the top of the hinged top lid 160 and into the rear of the housing via the top portion 158.

The control unit 200 is in the form of a box and has a control panel 202 on a forward sloping face. The unit contains a computer, which can regulate the flow rate of gas to the vessel via tube 102, as desired.

The control unit receives data during operation of the vessel 100 via data lines (not shown). Such data includes headspace pressure, pH of solution and oxygen saturation. The computer can govern the flow rate of gas to reach a desired set point in one of these parameters.

EXAMPLE

Growth of E. coli

Experimental conditions for all growth media and culture parameters were kept as similar as possible throughout.

Growth media: LB broth (Sigma L3022) was prepared to a concentration of 20 g/liter final concentration. Pre induction media was supplemented with 0.5% glucose to prevent leaky induction of the Lac promoter. All media contained ampicillin (Sigma A9518) to select for the recominant vector.

Cell Line chosen for protein expression was Merck Biosciences TUNER(DE3)™. This strain was transformed with the recombinant vector using the recommended protocol for this strain.

1 liter baffled flasks were used to grow cultures of 500 ml volume. Flasks were agitated vigorously at 225 rpm in a New Brunswick orbital shaker maintained at The 50 liter vessel shown in FIGS. 6 to 8 was part filled with deionised water which was fed directly into the bag through a Pall Kleenpak filter (Part Number KA3EKVP6G). A concentrate of LB media was added, followed by deionised water to make up the media to the final concentration. A 2 liter innoculum was added to the vessel, which had been grown-up overnight in four shaker flasks (500 ml in each).

Figure 9:
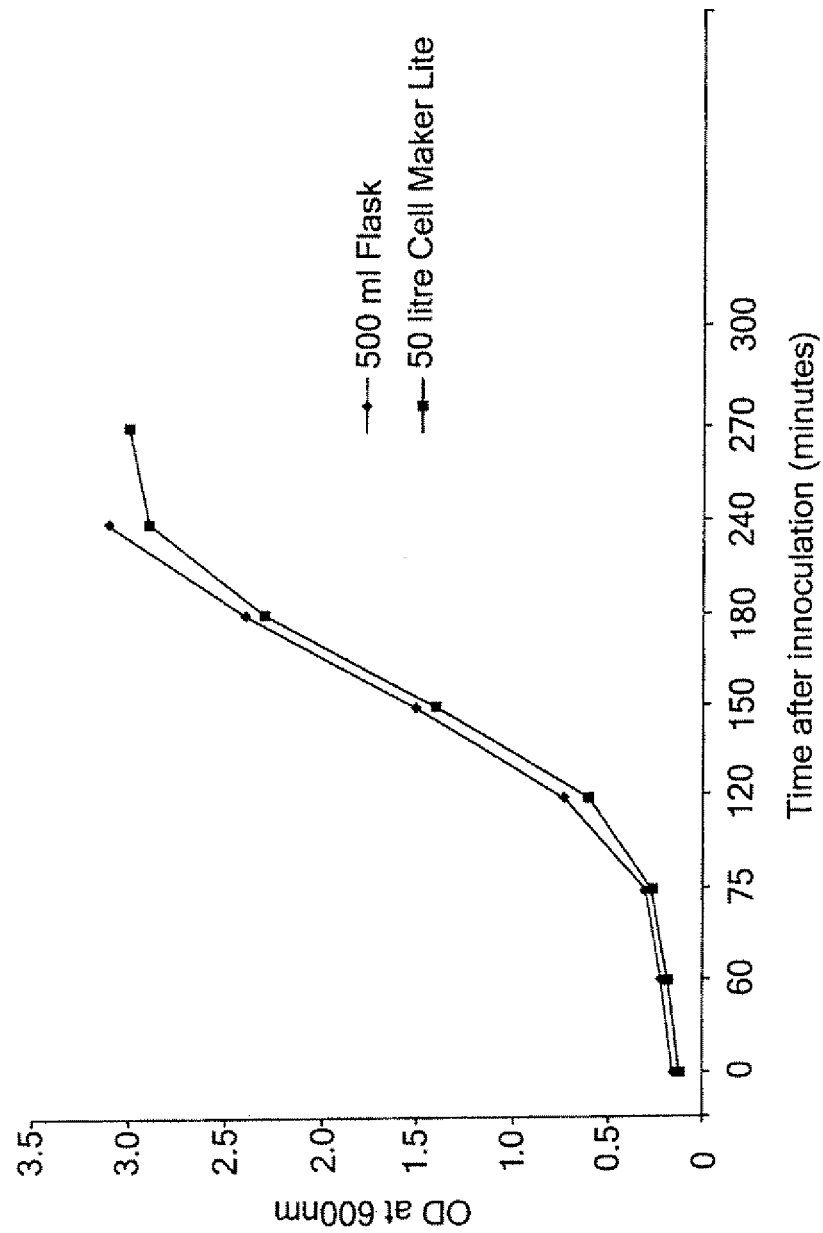
FIG. 9 is a graph of optical density (at 600 nm) versus time after innoculation (in minutes) of uninduced *E. coli* culture in a 500 ml bottled shaker flask and a 50 liter vessel according to the invention.
Figure 10:
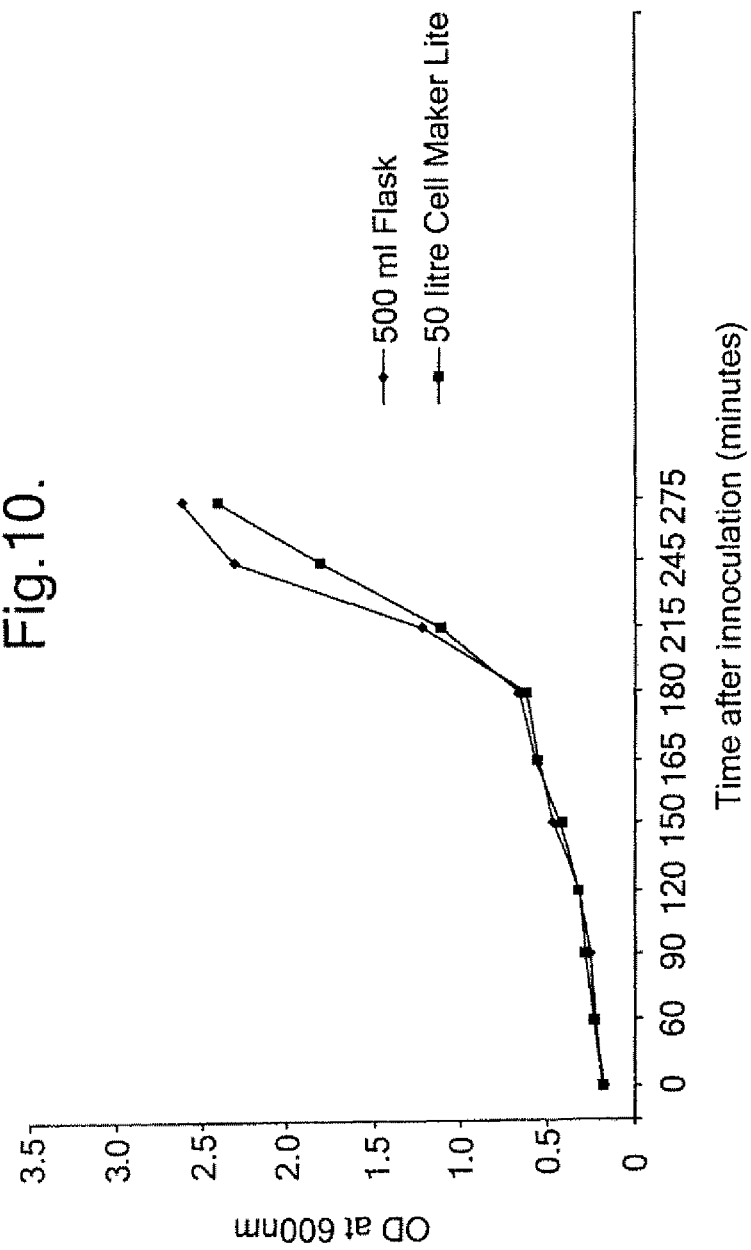
FIG. 10 is a graph similar to FIG. 9 showing optical density of *E. coli* culture induced with IPTG at OD 0.65 versus time for a cell culture in a 500 ml bottled shaker flask and a 50 liter vessel according to the invention.

The vessel according to the invention was used to culture E. coli cells to high cell densities and gave very comparable growth profiles to those generated in shaker flasks with vigorous agitation (FIGS. 9 and 10). Typically, disposable bioreactors are not used to grow E. coli due to the difficulties in achieving sufficient oxygen mass transfer, and as such, this was an excellent experimental model with which to demonstrate the system's efficient aeration process. The results indicate that growth curves and final densities that can be achieved in a 50 liter vessel are the same as a 500 ml culture in a flask. In the latter, the challenges of oxygen mass transfer are minimal.

FIGS. 9 and 10 also demonstrate that a 2 liter flask culture (4×500 ml) can be directly scaled-up to a 50 liter volume with no interim steps—a one-step scale-up was achieved.

The invention claimed is:

1. A cell culture and mixing vessel for containing a liquid, comprising
    a chamber having a lower chamber portion and an upper chamber portion wider than the lower chamber portion,
    a gas inlet for supplying gas to the lower chamber portion, the height of liquid being selectable such that when in use, liquid in the upper chamber portion circulates within the upper chamber portion as a result of the introduced gas and $G = (H \times A)/V$ is greater than 1.5, wherein A is the surface area of liquid in the vessel, H is the rise height of the gas and V is the volume of liquid,
    wherein the chamber has a front wall and a back wall,
    wherein when the back wall is vertically orientated, the front wall is inclined at an angle of incline, and
    wherein the angle of incline has an initial value which with increasing height is immediately followed by a reduction in the value of the angle of incline.

2. A vessel according to claim 1, wherein the reduction in the value of the angle of incline is in turn followed by an increase in the value of the angle of incline of the front wall.

3. A vessel according to claim 1, which further comprises an abutment for redirecting rising gas inclined with respect to the direction of rising gas, such that when in use, rising gas in the form of bubbles, initially rises substantially vertically in the liquid and is redirected in a substantially horizontal direction within the chamber by the abutment.

4. A vessel according to claim 3, wherein the chamber comprises
    a back wall, at least a part of which is vertical or substantially vertical, and
    a front wall.

5. A vessel according to claim 4, wherein the abutment is inclined relative to the vertical or substantially vertical part of the back wall.

6. A vessel according to claim 5, wherein the abutment is a non-vertical part of the back wall.

7. A vessel according to claim 1, wherein there is no physical barrier between any rising regions of liquid and any descending regions of liquid.

8. A vessel according to claim 4, wherein the gas inlet extends across substantially the whole length of the back wall.

9. A vessel according to claim 4, wherein at least part of the back wall is planar, and wherein the at least part of the back wall extending upwards from a level of the front wall at which the front wall has the initial value of angle of incline to a level at which the reduction in the angle of incline has occurred.

10. A vessel according to claim 1, wherein the widening of the vessel with respect to height occurs asymmetrically.

11. A vessel according to claim 1, wherein the lower chamber portion is tapered, becoming wider with increasing height.

12. A vessel according to claim 1, wherein at least a lower part of the upper chamber portion is tapered becoming wider with increasing height.

13. A vessel according to claim 1, which is made out of flexible plastics material.

14. A vessel according to claim 1, wherein the gas inlet comprises one or more tubes with a gas permeable wall.

15. A vessel according to claim 1, wherein the gas inlet has a plurality of exit holes, wherein each exit hole is of a size in a range of from 0.1 microns to 1 mm.

16. A vessel according to claim 1, further comprising a means for regulating the temperature of the liquid in the vessel.

17. A vessel according to claim 1, further comprising a means for providing a controllable pressure in gas above the liquid.

18. A vessel according to claim 1, arranged such that when in use, liquid in the upper chamber portion circulates within the upper chamber portion as a result of the introduced gas.

19. A mixing apparatus comprising a vessel according to claim 1.

20. A mixing apparatus according to claim 19, further comprising a separate controller device.

21. A vessel according to claim 1, wherein the reduction of the angle of incline is by at least 20°.

22. A vessel according to claim 15, in which each exit hole is of a size in a range of from 1 to 100 microns.

23. A method of performing a cell culture fermentation in a vessel, the vessel containing a liquid medium and cells to be cultured, and having a tapered lower chamber portion and a tapered upper chamber portion wider than the lower chamber portion, the method comprising the steps of filling the vessel with a volume V of liquid medium, thereby to obtain a surface area A of liquid in the vessel, and supplying a gas to the gas inlet of the vessel thereby to cause the gas to be admitted to the lower chamber portion to rise through a height H to the surface of the liquid and to cause liquid in the upper chamber portion to circulate within the upper chamber portion as a result of the introduced gas, wherein $G = (H \times A)/V$ is greater than 1.5, A being the surface area of liquid in the vessel, H the rise height of the gas in the liquid and V the volume of the liquid in the vessel.

24. A cell culture and mixing vessel, comprising a chamber having a tapered lower chamber portion and a tapered upper chamber portion wider than the lower chamber portion;

a gas inlet for supplying gas to liquid in the lower chamber portion; and an abutment with a structure sufficient to redirect rising gas in the form of bubbles, initially travelling substantially vertically, substantially horizontally within the chamber, wherein $G = (H \times A)/V$ is greater than 1.5, where A is the surface area of liquid in the vessel, H is the rise height of the gas and V is the volume of liquid, wherein the angle of the taper of the lower chamber portion is in the range of 5° to 40°, the angle of the taper of at least a lower part of the upper chamber portion is in the range of 25° to 80°, and wherein the lower part of the upper chamber portion has a smaller angle of inclination relative to the horizontal than the lower chamber portion.

* * * * *